US00PP29751P2

(12) United States Plant Patent
Lee

(10) Patent No.: US PP29,751 P2
(45) Date of Patent: Oct. 16, 2018

(54) ***HYDRANGEA* PLANT NAMED 'LEEP2'**

(50) Latin Name: *Hydrangea paniculata*
Varietal Denomination: LEEP2

(71) Applicant: Robert Edward Lee, Independence, LA (US)

(72) Inventor: Robert Edward Lee, Independence, LA (US)

(73) Assignee: Plant Development Services, Inc., Loxley, AL (US)

( * ) Notice: Subject to any disclaimer, the term of this patent is extended or adjusted under 35 U.S.C. 154(b) by 1 day.

(21) Appl. No.: 15/530,979

(22) Filed: Mar. 30, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

*Primary Examiner* — Anne Marie Grunberg
(74) *Attorney, Agent, or Firm* — Cassandra Bright

(57) ABSTRACT

A new and distinct *Hydrangea* cultivar named 'LEEP2' is disclosed, characterized by a large, conical inflorescence composed of clear white sterile flowers. Plants are mounding in habit, tolerate heat well and are easy to propagate. Branches are strong, reducing lodging over. The new variety is a *Hydrangea*, normally produced as an ornamental plant for containers or gardens

2 Drawing Sheets

Latin name of the genus and species: *Hydrangea paniculata.*

Variety denomination: 'LEEP2'.

BACKGROUND OF THE INVENTION

The new *Hydrangea* cultivar is a product of a planned breeding program conducted by the inventor in Independence, La. The objective of the breeding program was to produce new *Hydrangea paniculata* varieties for landscape use. The open pollination resulting in this new variety was made during 2007.

Seed was bulk collected from a variety of unpatented *Hydrangea paniculata* plants which had been open pollinated. The exact seed parent is unidentified. The pollen parent is unknown, as it was an open pollination breeding program. The new variety was identified as a potentially interesting selection in August of 2008, at a nursery in Independence, La.

Asexual reproduction of the new cultivar 'LEEP1' by softwood cuttings was first performed during the May of 2009, at commercial nursery in Independence, La. Subsequent propagation has shown that the unique features of this cultivar are stable and reproduced true to type in successive generations.

SUMMARY OF THE INVENTION

The cultivar 'LEEP2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LEEP2' These characteristics in combination distinguish 'LEEP2' as a new and distinct *Hydrangea* cultivar:

1. Long, conical inflorescence.
2. Thick branches, forming a sturdy, less floppy plant.

3. Mounding growth habit.
4. Heat tolerance.
5. Easy to propagate.
6. Clear white sterile flowers.

PARENT COMPARISON

The inventor cannot accurately identify seed and pollen parents.

COMMERCIAL COMPARISON

'LEEP2' are similar to plants of *Hydrangea paniculata* 'Phantom', unpatented in most horticultural characteristics, however, plants of the new cultivar 'LEEP2' differ in the following:

1. The new variety has thicker branches.
2. The new variety is smaller, reaching a height and width of approximately 6 to 8 feet, 'Phantom' reaches a mature height and width of approximately 6 to 10 feet.
3. Plants of the new variety are moderately dense, plants of 'Phantom' are loose and open.

'LEEP2' can be compared to the patented commercial variety *Hydrangea* 'Limelight' U.S. Plant Pat. No. 12,874. These varieties are similar in most horticultural characteristics, however 'LEEP2' differs in the following:

1. The new variety has a clearer white flower, with sepals colored near White 155A, the comparator has sepals colored near 145B and 145C.
2. The new variety has thicker branches.
3. Branches of the new variety are stiffer and less prone to lodging.

BRIEF DESCRIPTION OF THE PHOTOGRAPHS

Figure 1:
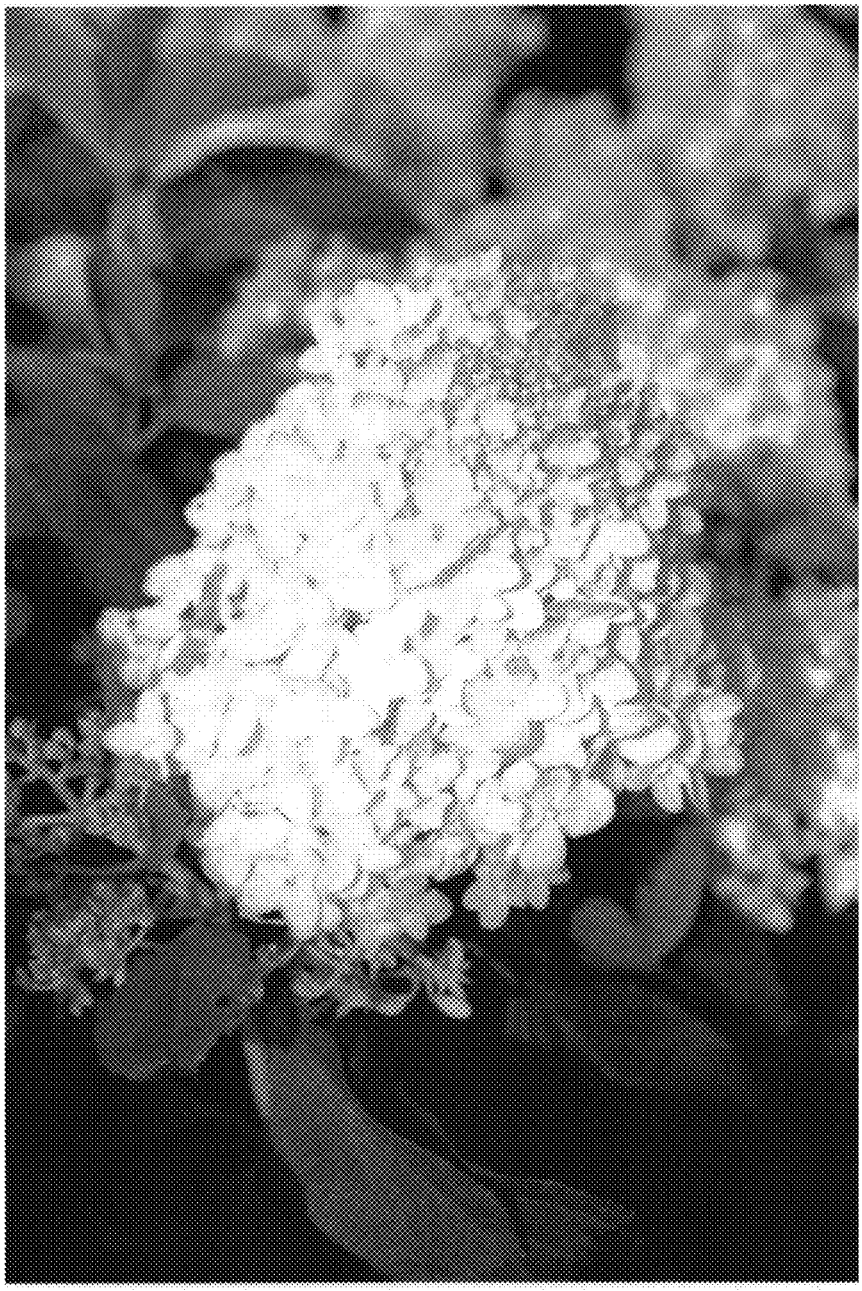

The accompanying photograph in FIG. 1 illustrates in full color a typical inflorescence of 'LEEP2'.

Figure 2:
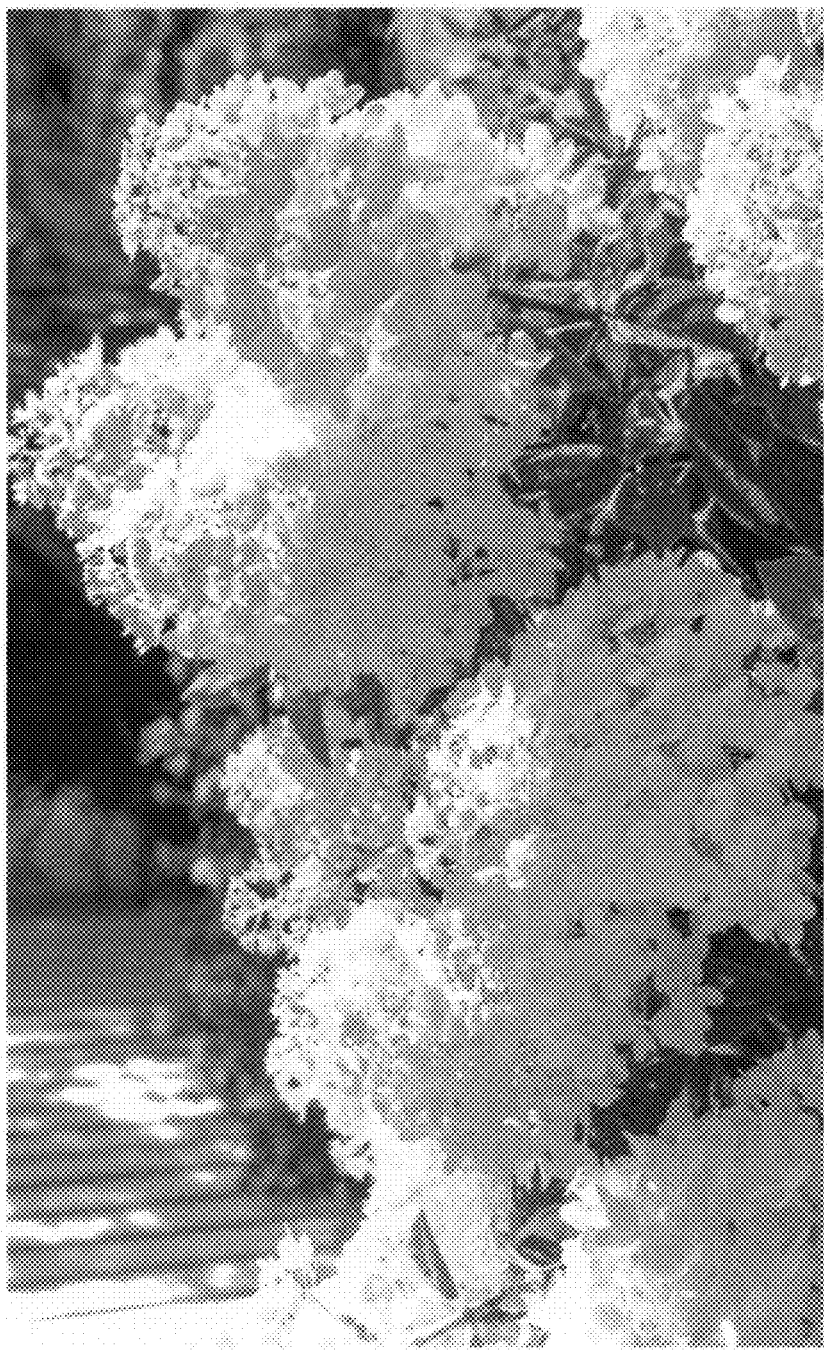

FIG. 2 illustrates multiple inflorescence on a flowering plant of 'LEEP2' grown in a outdoors in Loxley, Ala. Age of the plant photographed is approximately 2-3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2007 Royal Horticultural Society Colour Chart except where general terms of ordinary dictionary significance are used. The following observations and measurements describe 'LEEP2' plants outdoors, in Loxley, Ala. USA. The growing temperature ranged from approximately 18° C. to 27° C. daytime and 5° to 10° C. at night. Measurements and numerical values represent averages of typical plant types. Measurements were taken during August of 2016.

Botanical classification: *Hydrangea paniculata* 'LEEP2'.

PROPAGATION

Time to initiate roots: Approximately 18 days at approximately 27° C.

Time to produce a rooted young plants: Approximately 60 days at approximately 27° C.

Root description: Thick and fine, freely root branching and dense, fibrous. Color is white and brown, not accurately measured with an R.H.S. chart.

Propagation method: Softwood cuttings.

PLANT

Age of plant described: Approximately 2 years.

Pot size: 2 gallon.

Growth habit: Flowering perennial shrub, upright and round.

Overall plant shape: V-shaped.

Height: 46 cm.

Plant spread: 51 cm.

Growth rate: Good.

Plant vigor: Good.

Branching characteristics: Opposite, basal branches, some pinching required.

Length of lateral branches: Average 18 to 27 cm.

Number of lateral branches: 4 to 6 main branches, each with 2 to 6 lateral branches; after pinching.

Diameter of lateral branches: 7 mm.

Lateral branch shape and appearance: Round.

Lateral branch strength: Moderate.

Internode length: Average range 2.0 to 5.0 cm.

Branch color: Immature: Near RHS Yellow-Green 145C. Mature: Near RHS Greyed-Orange 177A and 177B, with infrequent streaks Greyed-Green 198A and 198B.

Branch angle: 15 to 35°.

Branch texture: Immature branches very short hirsute. Mature branches very slightly scaly.

FOLIAGE

Leaf:

*Arrangement*.—Opposite.

*Average length*.—9 to 12.5 cm.

*Average width*.—4.5 to 6.0 cm.

*Shape of blade*.—Ovate.

*Apex*.—Acute.

*Base*.—Rounded to truncate.

*Margin*.—Shallowly and sharply serrate, short apicular structure on serration.

*Texture and appearance of top surface*.—Short hirsute, matte.

*Texture and appearance of bottom surface*.—Matte, mainly glabrous. Few hirsute hairs on veins.

*Color*.—Young foliage upper side: Near RHS Green 143B. Young foliage under side: Near RHS Yellow-Green 144B. Mature foliage upper side: Near RHS Green 137A. Mature foliage under side: Near RHS Green 138B.

*Venation*.—Type: Pinnate. Venation color upper side: Near RHS Yellow-Green 145B. Venation color under side: Near RHS Yellow-Green 145B.

Petiole:

*Average length*.—2.5 cm.

*Diameter*.—4 mm.

*Color*.—Upper side: Near RHS Yellow-green 145B. Under side: Near RHS Yellow-green 145B.

*Texture upper side*.—Hirsute.

*Texture under side*.—Hirsute.

FLOWER

Bloom period:

*Natural season*.—Early Summer until Fall.

Inflorescence:

*Arrangement*.—Terminal corymb.

*Commercial type*.—Mophead.

*Infloresence shape*.—Conical.

*Panicle height*.—15 to 20 cm.

*Panicle diameter*.—7-15 cm.

*Panicle shape*.—

*Quantity of flowers per inflorescence*.—Fertile flowers not observed to date. Sterile Flowers, 200 to 350 approximate average.

*Persistent or self-cleaning*.—Self-cleaning.

*Fragrance*.—None.

Sterile flower:

*Bud shape*.—Obovate.

*Bud length*.—3.0 mm.

*Bud diameter*.—5.0 mm.

*Bud color*.—Near RHS Yellow-Green 150D.

*Flower aspect*.—Upright and outward.

*Flower shape*.—Cruciform.

*Flower diameter*.—Average range 22 to 29 mm.

*Flower depth*.—10 mm.

*Aspect*.—Facing upright and outward.

Sterile flower sepals:

*Petal arrangement*.—Cruciform.

*Petal number*.—4, occasionally 5.

*Length of petal*.—Approximately 8 to 12 mm.

*Width of petal*.—Approximately 9 to 11 mm.

*Angel of attachment/aspect*.—Petals angled upward approximately 15° to 25° from point of attachment. Petals upwardly cupped.

*Apex*.—Rounded.

*Shape of petal*.—Ovate.

*Petal margin*.—Entire.

*Petal base*.—Obtuse.

*Petal texture*.—Smooth, upper and under sides.

*Color*.—Upper surface at first opening: Near RHS Yellow-Green 150D. Upper surface at maturity: Near RHS White 155A. Under surface at first opening: Near RHS Yellow-Green 150D. Under surface at maturity: Near RHS White 155A. Color when fading: Upper and lower surfaces: Near RHS Yellow-Green 145D.

Sterile flower petal: Highly reduced structure.

*Arrangement*.—Whorl.

*Number*.—4.

*Shape*.—Ovate.

*Tip*.—Rounded.

*Base*.—Truncate.

*Margin*.—Entire.

*Length*.—1.5 mm.

*Width*.—1 mm.

*Texture, upper*.—Smooth.

*Texture, lower*.—Smooth.

*Color*.—All surfaces at first opening: Near RHS Yellow-Green 150D. All surfaces at maturity: Near RHS Yellow-Green 150D. All surfaces fading to: Near RHS Yellow-Green 150D.

Sterile flower pedicel:

*Length*.—10 to 17 mm.

*Diameter*.—1 mm.

*Angle*.—Upright and outward.

*Strength*.—Flexible, not prone to breakage.

*Texture*.—Smooth.

*Color*.—Near RHS Yellow-Green 145D.

Fertile flower: Not observed to date.

REPRODUCTIVE ORGANS

Sterile flower: All reproductive parts reduced to less than 1 mm or not present.

*Stamen number*.—3 or 4.

*Filament length*.—Average 1 mm.

*Filament color*.—Near RHS Yellow-Green 150D.

*Anther shape*.—Oblong and irregularly lobed.

*Anther length*.—0.5 mm.

*Anther color*.—Near RHS Yellow-Green 145B.

*Pollen amount*.—None.

*Gynoecium*.—Not present, or reduced beyond recognition.

*Pistil number*.—1.

OTHER CHARACTERISTICS

Disease resistance: Neither resistance nor susceptibility to diseases or pests has been observed in this variety.

Temperature tolerance: USDA Zones 3 through 8.

Fruit/seed production: Seed production not observed to date.

What is claimed is:

1. A new and distinct cultivar of *Hydrangea* plant named 'LEEP2' as herein illustrated and described.

* * * * *